US009056808B2

(12) United States Patent
Tirtowidjojo et al.

(10) Patent No.: US 9,056,808 B2
(45) Date of Patent: Jun. 16, 2015

(54) PROCESS FOR THE PRODUCTION OF CHLORINATED PROPENES

(75) Inventors: Max M. Tirtowidjojo, Lake Jackson, TX (US); William J. Kruper, Jr., Sanford, MI (US); Barry B. Fish, Lake Jackson, TX (US); David S. Laitar, Midland, MI (US)

(73) Assignee: Dow Global Technologies, LLC, Midland, MI (US)

( * ) Notice: Subject to any disclaimer, the term of this patent is extended or adjusted under 35 U.S.C. 154(b) by 29 days.

(21) Appl. No.: 14/123,139

(22) PCT Filed: May 18, 2012

(86) PCT No.: PCT/US2012/038613
§ 371 (c)(1),
(2), (4) Date: Nov. 29, 2013

(87) PCT Pub. No.: WO2012/166394
PCT Pub. Date: Dec. 6, 2012

(65) Prior Publication Data
US 2014/0081055 A1    Mar. 20, 2014

Related U.S. Application Data

(60) Provisional application No. 61/491,816, filed on May 31, 2011.

(51) Int. Cl.
*C07C 17/10*   (2006.01)
*C07C 17/25*   (2006.01)
*C07C 21/04*   (2006.01)

(52) U.S. Cl.
CPC ............... *C07C 17/25* (2013.01); *C07C 17/10* (2013.01)

(58) Field of Classification Search
USPC .......................................... 570/226, 230, 229
See application file for complete search history.

(56) References Cited

U.S. PATENT DOCUMENTS 2,119,484 A    5/1938   Levine
2,179,378 A    11/1939  Metzger
(Continued)

FOREIGN PATENT DOCUMENTS

CH    609022       6/1974
CN    101492341    7/2009
(Continued)

OTHER PUBLICATIONS

Fields et al., "Thermal Isomerization of 1,1-dichlorocyclopropanes", Chemical Communications (London) No. 21, Jan. 1, 1967, p. 1081.
(Continued)

*Primary Examiner* — Jafar Parsa
*Assistant Examiner* — Medhanit Bahta
(74) *Attorney, Agent, or Firm* — Susan M. Zerull; KSJLAW, LLC (57) ABSTRACT

Processes for the production of chlorinated propenes are provided. The present processes make use of 1,2-dichloropropane, a by-product in the production of chlorohydrin, as a low cost starting material, alone or in combination with 1,2,3-trichloropropane. The present processes can also generate anhydrous HCl as a byproduct that can be removed from the process and used as a feedstock for other processes, providing further time and cost savings. Finally, the processes are advantageously conducted in the liquid phase, thereby presenting additional savings as compared to conventional, gas phase processes.

15 Claims, 6 Drawing Sheets

(56) References Cited

U.S. PATENT DOCUMENTS

| | | |
|---|---|---|
| 2,207,193 A | 7/1940 | Groll |
| 2,299,441 A | 10/1942 | Vaughan |
| 2,302,228 A | 11/1942 | Kharasch |
| 2,370,342 A | 2/1945 | Zellner |
| 2,378,859 A | 6/1945 | Martin |
| 2,435,983 A | 2/1948 | Schmerling |
| 2,449,286 A | 9/1948 | Fairbairn |
| 2,588,867 A | 3/1952 | Morris |
| 2,630,461 A | 3/1953 | Sachsse |
| 2,688,592 A | 9/1954 | Skeeters |
| 2,762,611 A | 9/1956 | Monroe |
| 2,765,359 A | 10/1956 | Pichler |
| 2,964,579 A | 12/1960 | Weller et al. |
| 2,973,393 A | 2/1961 | Monroe |
| 3,000,980 A | 9/1961 | Asadorian |
| 3,094,567 A | 6/1963 | Eaker |
| 3,112,988 A | 12/1963 | Coldren et al. |
| 3,444,263 A | 5/1969 | Fernald |
| 3,446,859 A | 5/1969 | Weil |
| 3,502,734 A | 3/1970 | Baird |
| 3,525,595 A | 8/1970 | Zirngibl et al. |
| 3,551,512 A | 12/1970 | Loeffler |
| 3,558,438 A | 1/1971 | Schoenbeck |
| 3,651,019 A | 3/1972 | Asscher |
| 3,676,508 A | 7/1972 | Krekeler |
| 3,819,731 A | 6/1974 | Pitt |
| 3,823,195 A | 7/1974 | Smith |
| 3,872,664 A | 3/1975 | Lohmann |
| 3,914,167 A | 10/1975 | Ivy |
| 3,926,758 A | 12/1975 | Smith |
| 3,948,858 A | 4/1976 | Wiersum |
| 3,954,410 A | 5/1976 | Pohl |
| 4,038,372 A | 7/1977 | Colli |
| 4,051,182 A | 9/1977 | Pitt |
| 4,319,062 A | 3/1982 | Boozalis et al. |
| 4,513,154 A | 4/1985 | Kurtz |
| 4,535,194 A | 8/1985 | Woodard |
| 4,614,572 A | 9/1986 | Holbrook |
| 4,644,907 A | 2/1987 | Hunter |
| 4,650,914 A | 3/1987 | Woodard |
| 4,661,648 A | 4/1987 | Franklin |
| 4,702,809 A | 10/1987 | Mueller |
| 4,714,792 A | 12/1987 | Muller |
| 4,716,255 A | 12/1987 | Muller |
| 4,726,686 A | 2/1988 | Wolf |
| 4,727,181 A | 2/1988 | Kruper |
| 4,849,554 A | 7/1989 | Cresswell et al. |
| 4,894,205 A | 1/1990 | Westerman |
| 4,902,393 A | 2/1990 | Muller |
| 4,999,102 A | 3/1991 | Cox |
| 5,057,634 A | 10/1991 | Webster |
| 5,132,473 A | 7/1992 | Furutaka |
| 5,171,899 A | 12/1992 | Furutaka |
| 5,178,844 A | 1/1993 | Carter et al. |
| 5,254,771 A | 10/1993 | Cremer |
| 5,254,772 A | 10/1993 | Dukat |
| 5,254,788 A | 10/1993 | Gartside |
| 5,262,575 A | 11/1993 | Dianis |
| 5,315,044 A | 5/1994 | Furutaka |
| 5,367,105 A | 11/1994 | Miyazaki et al. |
| 5,414,166 A | 5/1995 | Kim |
| 5,504,266 A | 4/1996 | Tirtowidjojo et al. |
| 5,614,323 A | 3/1997 | Chang |
| 5,684,219 A | 11/1997 | Boyce |
| 5,689,020 A | 11/1997 | Boyce |
| 5,811,605 A | 9/1998 | Tang |
| 5,895,825 A | 4/1999 | Elsheikh |
| 5,986,151 A | 11/1999 | Van Der Puy |
| 6,111,150 A | 8/2000 | Sakyu |
| 6,118,018 A | 9/2000 | Savidakis |
| 6,160,187 A | 12/2000 | Strickler |
| 6,187,976 B1 | 2/2001 | Van Der Puy |
| 6,229,057 B1 | 5/2001 | Jackson et al. |
| 6,235,951 B1 | 5/2001 | Sakyu et al. |
| 6,472,573 B1 | 10/2002 | Yamamoto |
| 6,518,467 B2 | 2/2003 | Tung et al. |
| 6,538,167 B1 | 3/2003 | Brown |
| 6,545,176 B1 | 4/2003 | Tsay |
| 6,551,469 B1 | 4/2003 | Nair |
| 6,610,177 B2 | 8/2003 | Tsay |
| 6,683,216 B1 | 1/2004 | Zoeller |
| 6,825,383 B1 | 11/2004 | Dewkar |
| 6,924,403 B2 | 8/2005 | Barnes et al. |
| 6,958,135 B1 | 10/2005 | Filippi |
| 7,117,934 B2 | 10/2006 | Lomax |
| 7,189,884 B2 | 3/2007 | Mukhopadhyay |
| 7,226,567 B1 | 6/2007 | Olbert |
| 7,282,120 B2 | 10/2007 | Braun |
| 7,297,814 B2 | 11/2007 | Yada |
| 7,345,209 B2 | 3/2008 | Mukhopadhyay |
| 7,371,904 B2 | 5/2008 | Ma |
| 7,378,559 B2 | 5/2008 | Verwijs |
| 7,396,965 B2 | 7/2008 | Mukhopadhyay |
| 7,511,101 B2 | 3/2009 | Nguyen |
| 7,521,029 B2 | 4/2009 | Guetlhuber |
| 7,588,739 B2 | 9/2009 | Sugiyama |
| 7,659,434 B2 | 2/2010 | Mukhopadhyay |
| 7,674,939 B2 | 3/2010 | Mukhopadhyay |
| 7,687,670 B2 | 3/2010 | Nappa |
| 7,695,695 B2 | 4/2010 | Shin |
| 7,714,177 B2 | 5/2010 | Mukhopadhyay |
| 7,836,941 B2 | 11/2010 | Song |
| 7,880,040 B2 | 2/2011 | Mukhopadhyay |
| 7,951,982 B2 | 5/2011 | Mukhopadhyay |
| 8,058,486 B2 | 11/2011 | Merkel |
| 8,058,490 B2 | 11/2011 | Strebelle |
| 8,071,825 B2 | 12/2011 | Johnson |
| 8,071,826 B2 | 12/2011 | Van Der Puy |
| 8,076,521 B2 | 12/2011 | Elsheikh |
| 8,084,653 B2 | 12/2011 | Tung |
| 8,115,038 B2 | 2/2012 | Wilson |
| 8,123,398 B2 | 2/2012 | Teshima |
| 8,158,836 B2 | 4/2012 | Pigamo |
| 8,232,435 B2 | 7/2012 | Sievert |
| 8,258,353 B2 | 9/2012 | Kruper |
| 8,258,355 B2 | 9/2012 | Merkel |
| 8,357,828 B2 | 1/2013 | Okamoto |
| 8,367,867 B2 | 2/2013 | Zardi |
| 8,383,867 B2 | 2/2013 | Mukhopadhyay |
| 8,395,000 B2 | 3/2013 | Mukhopadhyay |
| 8,398,882 B2 | 3/2013 | Rao |
| 8,487,146 B2 | 7/2013 | Wilson |
| 8,581,011 B2 | 11/2013 | Tirtowidjojo |
| 8,581,012 B2 | 11/2013 | Tirtowidjojo et al. |
| 8,614,361 B2 | 12/2013 | Suzuki |
| 2001/0018962 A1 | 9/2001 | Joshi |
| 2002/0110711 A1 | 8/2002 | Boneberg |
| 2006/0150445 A1 | 7/2006 | Redding |
| 2006/0292046 A1 | 12/2006 | Fruchey |
| 2007/0197841 A1 | 8/2007 | Mukhopadhyay |
| 2007/0197842 A1* | 8/2007 | Mukhopadhyay et al. ... 570/155 |
| 2007/0265368 A1 | 11/2007 | Rao |
| 2008/0021229 A1 | 1/2008 | Maughon |
| 2008/0073063 A1 | 3/2008 | Clavenna et al. |
| 2008/0118018 A1 | 5/2008 | Schrauwen |
| 2008/0207962 A1 | 8/2008 | Rao |
| 2009/0018377 A1 | 1/2009 | Boyce |
| 2009/0099396 A1 | 4/2009 | Mukhopadhyay |
| 2009/0117014 A1 | 5/2009 | Carpenter |
| 2009/0203945 A1 | 8/2009 | Mukhopadhyay |
| 2010/0041864 A1 | 2/2010 | Kadowaki et al. |
| 2010/0185029 A1 | 7/2010 | Elsheikh |
| 2010/0263278 A1 | 10/2010 | Kowoll et al. |
| 2011/0172472 A1 | 7/2011 | Sakyu |
| 2011/0218369 A1 | 9/2011 | Elsheikh |
| 2011/0251425 A1 | 10/2011 | Penzel |
| 2012/0065434 A1 | 3/2012 | Nose |
| 2014/0081055 A1 | 3/2014 | Tirtowidjojo |

FOREIGN PATENT DOCUMENTS

| | | |
|---|---|---|
| CN | 101544535 | 9/2009 |
| CN | 101597209 | 12/2009 |
| CN | 101913979 | 12/2010 |

(56) References Cited

FOREIGN PATENT DOCUMENTS

| | | |
|---|---|---|
| CN | 101913980 | 12/2010 |
| CN | 101955414 | 1/2011 |
| CN | 101982227 | 3/2011 |
| CN | 102001911 | 4/2011 |
| CN | 102249846 | 11/2011 |
| CN | 102351637 | 2/2012 |
| DE | 857955 | 12/1952 |
| DE | 209184 | 4/1984 |
| DE | 235631 | 5/1986 |
| DE | 102005044501 | 3/2007 |
| DE | 102010022414 | 12/2011 |
| EP | 0164798 | 12/1985 |
| EP | 0453818 | 10/1991 |
| EP | 1018366 | 12/2000 |
| EP | 1097984 A1 | 5/2001 |
| FR | 1546709 | 11/1968 |
| GB | 471186 | 8/1937 |
| GB | 471187 | 8/1937 |
| GB | 471188 | 8/1937 |
| GB | 857086 | 12/1960 |
| GB | 1134585 | 11/1968 |
| GB | 1381619 | 1/1975 |
| GB | 1548277 | 7/1979 |
| JP | 54-079207 | 6/1979 |
| JP | S54-135712 | 10/1979 |
| JP | 08-119885 | 5/1996 |
| JP | 2001-151708 | 6/2001 |
| JP | 2001-213820 | 8/2001 |
| JP | 2006-272267 A | 10/2006 |
| JP | 2007-021396 | 2/2007 |
| JP | 2008-063314 | 3/2008 |
| JP | 2009-000592 A | 1/2009 |
| JP | 2009-046653 | 3/2009 |
| JP | 2011-144148 | 7/2011 |
| LU | 52247 | 12/1966 |
| SU | 899523 | 1/1982 |
| WO | 0138271 | 5/2001 |
| WO | 0138275 | 5/2001 |
| WO | 02059536 A1 | 8/2002 |
| WO | 2005016509 | 2/2005 |
| WO | 2007079431 | 7/2007 |
| WO | 2007079435 | 7/2007 |
| WO | 2007096383 | 8/2007 |
| WO | 2009015304 | 1/2009 |
| WO | 2009067571 | 5/2009 |
| WO | 2009087423 | 7/2009 |
| WO | 2011060211 | 5/2011 |
| WO | 2011065574 | 6/2011 |
| WO | 2012011844 | 1/2012 |
| WO | 2012081482 | 6/2012 |
| WO | 2012166393 | 12/2012 |

OTHER PUBLICATIONS

Nguyen et al., Condensation de chloroforme avec des olefins fluorees en milieu basique, Journal of Fluorine Chemistry, vol. 55, No. 3, Dec. 1, 1991, pp. 241-248.
Shelton et al., "Addition of Halogens and Halogen Compounds to Allylic Chlorides. I. Addition of Hydrogen Halides", Journal of Organic Chemistry, Sep. 1958, pp. 1876-1880, vol. 23.
Tobey et al., "Pentachlorocyclopropane 1" Journal of the American Chemical Society, vol. 88, No. 11, Jun. 1, 1996 pp. 2478-2481.
Ochi, et al., "Preparation of Chloropropenes by Photochemical Dehydrochlorination of 1,2-Dichloropropane", Chemical Abstracts, Jul. 17, 1989, p. 574, 111(3).
Stevens, "Some New Cyclopropanes with a Note on the Exterior Valence Angles of Cyclopropane", JACS, vol. 68, No. 4, 1945, 620-622.
Bai et al., "Isomerization of Tetrachloropropene to Promote Utilization Ratio of Triallate Raw Materials", Petrochemical Technology & Application, 2007, 25(1).
Boualy et al., "Kharasch Addition of Tetrachloromethane to Alkenes Catalyzed by Metal Acetylacetonates", Catalysis Communications, 2011, pp. 1295-1297, vol. 12.
Chai et al., "Study of Preparation of 1,1,1,3-tetrachloropropane", Zhejiang Chemical Industry, 2010, pp. 1-3, 41(5).
Cristiano et al., "Tetraalkylphosphonium Trihalides. Room Temperature Ionic Liquids As Halogenation Reagents", J. Org. Chem., 2009, pp. 9027-9033, vol. 74.
Evstigneev et al., "Initiated Chlorination of Tetrachloropropane", Khim. Prom., 1984, pp. 393-394, 16(7).
Galitzenstein et al., "The Dehydrochlorination of Propylene Dichloride", Journal of the Society of Chemical Industry, 1950, pp. 298-304, vol. 69.
Gault et al., "Chlorination of Chloroform", Comptes Rendus Des Seances De L'Academie des Sciences, 1924, pp. 467-469, vol. 179.
Gerding et al., "Raman Spectra of aliphatic chlorine compounds II. Chloroethenes and Chloropropenes", Recueil, Jan. 1, 1955, pp. 957-975, vol. 74.
Hatch et al., "Allylic Chlorides. XV. Preparation and Properties of the 1,2,3-Trichloropropenes", JACS, Jan. 5, 1952, pp. 123-126, 74(1).
Hatch et al., "Allylic Chlorides. XVIII. Preparation and Properties of 1,1,3-tricholoro-2-fluoro-1-propene and 1,1,2,3-tetrachloro-1-propene", JACS, Jul. 5, 1952, pp. 3328-3330, 74(13).
Herzfelder, "Substitution in the Aliphatic Series", Berichte der Deutschen Chemischen Gesellschaft, May-Aug. 1893, pp. 1257-1261, 26(2).
Ivanov et al., "Metal Phthalocyanine-Catalyzed Addition of Polychlorine-Containing Organic Compounds to C=C Bonds", Russian Chemical Bulletin, International Edition, Nov. 2009, pp. 2393-2396, 58(11).
Kang et al., "Kinetics of Synthesis of 1,1,1,3,3-pentachlorobutane Catalyzed by Fe—FeCl3", Chemical Research and Application, Jun. 2011, pp. 657-660, 23(6).
Kharasch et al., "Chlorinations with Sulfuryl Chloride. I. The Peroxide-Catalyzed Chlorination of Hydrocarbons", JACS, 1939, pp. 2142-2150, vol. 61.
Khusnutdinov et al., "CCl4 Attachment to Olefins Catalyzed by Chromium and Ruthenium Complexes. Impact of Water as a Nucleophilic Admixture", Oil Chemistry, 2009, pp. 349-356, vol. 4.
Kruper et al., "Synthesis of alpha-Halocinnamate Esters via Solvolytic Rearrangement of Trichloroallyl Alcohols", J. Org. Chem., 1991, pp. 3323-3329, vol. 56.
Leitch, "Organic Deuterium Compounds: V. The chlorination of propyne and propyne D-4", Canadian Journal of Chemistry, Apr. 1, 1953, pp. 385-386, 30(4).
Levanova et al., "Thermocatalytic Reactions of Bromochloropropanes", Russian Journal of Physical Chemistry, Jan. 1, 1983, pp. 1142-1146, vol. 57.
Liu et al., "Progress in the Synthesis of 1,1,1,3-tetrachloropropane", Guangzhou Chemicals, 2011, pp. 41-42, 39(5).
McBee et al., "Utilization of Polychloropropanes and Hexachloroethane", Industrial and Engineering Chemistry, Feb. 1, 1941, pp. 176-181, 33(2).
Mouneyrat, "Effect of Chlorine on Propyl Chloride in the Presence of Anhydrous Aluminum Chloride" Bulletin de la Societe Chimique de Paris, Jan. 1, 1899, pp. 616-623, 3(21).
Munoz-Molina et al., "An Efficient, Selective and Reducing Agent-Free Copper Catalyst for the Atom-Transfer Radical Addition of Halo Compounds to Activated Olefins", Inorg. Chem., 2010, pp. 643-645, 49.
Nair et al., "Atom Transfer Radical Addition (ATRA) of Carbon Tetrachloride and Chlorinated Esters to Various Olefins Catalyzed by CP'Ru(PPh3)(PR3)Cl Complexes", Inorganica Chimica Acta, 2012, pp. 96-103, vol. 380.
Nikishin et al., "Reactions of Methanol and Ethanol", Seriya Khimicheskaya, Dec. 1966, pp. 2188-2192, vol. 12.
Pozdnev et al., "Chlorination of Chloroform and the Conversion of Methylene Chloride Manufacture Still Residues", Khim., Khim. Tekhnol., 1970, 70(4).
Rotshtein et al., "Isomer Distribution on Chlorination of Chloropropanes", Zhurnal Organicheskoi Khimii, Sep. 1966, pp. 1539-1542, 2(9).
Semenov et al., "Selectivity of Photochemical Chlorination of Chloromethane in the Liquid Phase", Zhurnal Prikladnoi Khimii, Apr. 1985, pp. 840-845, 58(4).

(56) References Cited

OTHER PUBLICATIONS

Skell et al., "Reactions of BrCl with Alkyl Radicals", Tetrahedron Letters, 1986, pp. 5181-5184, 27(43).

Skell et al., "Selectivities of pi and sigma-Succinimidyl Radicals in Aubstitution and Addition Reactions. Appendix: Response to Walling, El-Taliawi and Zhao", JACS, Jul. 1, 1983, pp. 5125-5131, 105(15).

Tanuma et al., "Partially Fluorinated Metal Oxide Catalysts for a Friedel-Crafts-type Reaction of Dichlorofluoromethane with Tetrafluoroethylene", Catalysis Letters, 2010, pp. 77-82, vol. 136.

Urry et al., "Free-Radical Reactions of Diazomethane with Reactive Bromopolychloroalkanes", JACS, May 5, 1964, pp. 1815-1819, 86(9).

Wang, "Elimination Reactions of Polyhalopropanes under Emulsion Catalytic Conditions to give Halopropenes", Synthesis, Jun. 1982, pp. 494-496, vol. 6.

Zhao et al., "Research Progress on Preparation Technology of 1,1,2,3-Tetrachloropropene", Zhejiang Chemical Industry, 2010, pp. 8-10, 41(8).

Zheng et al., "Review of the Preparation of the low GWP alternative 1,3,3,3-tetrafluoropropene", Zhejiang Chemical Industry, 2010, pp. 5-7, 41(3).

* cited by examiner

PROCESS FOR THE PRODUCTION OF CHLORINATED PROPENES

FIELD

The present invention relates to processes for the production of chlorinated propenes.

BACKGROUND

Hydrofluorocarbon (HFC) products are widely utilized in many applications, including refrigeration, air conditioning, foam expansion, and as propellants for aerosol products including medical aerosol devices. Although HFC's have proven to be more climate friendly than the chlorofluorocarbon and hydrochlorofluorocarbon products that they replaced, it has now been discovered that they exhibit an appreciable global warming potential (GWP).

The search for more acceptable alternatives to current fluorocarbon products has led to the emergence of hydrofluoroolefin (HFO) products. Relative to their predecessors, HFOs are expected to exert less impact on the atmosphere in the form of a lesser, or no, detrimental impact on the ozone layer and their much lower GWP as compared to HFC's. Advantageously, HFO's also exhibit low flammability and low toxicity.

As the environmental, and thus, economic importance of HFO's has developed, so has the demand for precursors utilized in their production. Many desirable HFO compounds, e.g., such as 2,3,3,3-tetrafluoroprop-1-ene or 1,3,3,3-tetrafluoroprop-1-ene, may typically be produced utilizing feedstocks of chlorocarbons, and in particular, chlorinated propenes, which may also find use as feedstocks for the manufacture of polyurethane blowing agents, biocides and polymers.

Unfortunately, many chlorinated propenes may have limited commercial availability, and/or may only be available at prohibitively high cost, due at least in part to the complicated, multi-step processes typically utilized in their manufacture. This may be due at least in part to the fact that conventional processes for their manufacture may require the use of starting materials that are prohibitively expensive to be economically produced by manufacturers on the large scale required to be useful as feedstocks. Additionally, conventional processes may require multiple chlorination and dehydrochlorination steps to arrive at a desired level of chlorination in the final product. Dehydrochlorination steps are typically conducted with an aqueous base, and result in the production of large quantites of waste water containing large quantities of sodium chloride and/or chlorinated organics. Treatment of this waste water is time consuming and expensive, and results in the recovery of low value by-products.

It would thus be desirable to provide improved processes for the large capacity and/or continuous production of chlorocarbon precursors useful as feedstocks in the synthesis of refrigerants and other commercial products. More particularly, such processes would provide an improvement over the current state of the art if they were less costly in starting materials, processing time, and/or capital costs required to implement and maintain the process. Generation of byproducts having a higher value than sodium chloride, or really any value, would be a further advantage if provided in such a process.

BRIEF DESCRIPTION

The present invention provides efficient processes for the production of chlorinated propenes. Advantageously, the processes make use of 1,2-dichloropropane, a by-product in the production of chlorohydrin, as a low cost starting material, alone or in combination with 1,2,3-trichloropropane. Selectivity of the process is enhanced over conventional chlorination processes by employing successive chlorination steps, using an ionic chlorination catalyst, and dehydrochlorination steps. Because 1,2-dichloropropane and 1,2,3-trichloropropane are directly chlorinated to chlorinated propene isomers, fewer steps are required than conventional processes, and capital cost and time savings are provided. Further, since lesser amounts of chlorinated propane intermediates are processed through caustic cracking, anhydrous HCl can be recovered from the process rather than the lower value NaCl produced by multiple caustic cracking steps. Less waste water is thus generated, providing further time and cost savings.

In one aspect, the present invention provides a process for the production of chlorinated propenes from one or more chlorinated alkanes. The process comprises at least one liquid phase chlorination step conducted in the presence of a free radical initiator and at least one dehydrochlorination step. The one or more chlorinated alkanes comprise 1,2-dichloropropane, and may further comprise1,2,3-trichloropropane. The chlorination agent comprises chlorine, $SO_2Cl_2$, or combinations of these. The free radical initiator desirably comprises azobisisobutyronitrile (AIBN), 2,2'-azobis(2,4-dimethyl valeronitrile, dimethyl 2,2'-azobis(2-methylpropionate), 1,1'-azobis(cyclohexane-1-carbonitrile) or 1,1'-azobis(cyclohexanecarbonitrile (ABCN), ultraviolet light or combinations of these. The chlorinated propene produced desirably comprises from 3 to 5 chlorine atoms, and in some embodiments, may be 1,1,2,3-tetrachloropropene. HCl is generated by the process as a by-product, and in some embodiments, may be recovered in its anhydrous form for use, e.g., in downstream processes. Further, one or more reactants may be generated within or upstream of the process.

The advantages provided by the present processes may be carried forward by utilizing the chlorinated propenes to produce further downstream products, such as, e.g., 2,3,3,3-tetrafluoroprop-1-ene or 1,3,3,3-tetrafluoroprop-1-ene.

DETAILED DESCRIPTION

The present specification provides certain definitions and methods to better define the present invention and to guide those of ordinary skill in the art in the practice of the present invention. Provision, or lack of the provision, of a definition for a particular term or phrase is not meant to imply any particular importance, or lack thereof. Rather, and unless otherwise noted, terms are to be understood according to conventional usage by those of ordinary skill in the relevant art.

The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced item, and the terms "front", "back", "bottom", and/or "top", unless otherwise noted, are merely used for convenience of description, and are not limited to any one position or spatial orientation.

If ranges are disclosed, the endpoints of all ranges directed to the same component or property are inclusive and independently combinable (e.g., ranges of "up to 25 wt. %, or, more specifically, 5 wt. % to 20 wt. %," is inclusive of the endpoints and all intermediate values of the ranges of "5 wt. % to 25 wt. %," etc.). As used herein, percent (%) conversion is meant to indicate change in molar or mass flow of reactant in a reactor in ratio to the incoming flow, while percent (%) selectivity means the change in molar flow rate of product in a reactor in ratio to the change of molar flow rate of a reactant.

Reference throughout the specification to "one embodiment" or "an embodiment" means that a particular feature, structure, or characteristic described in connection with an embodiment is included in at least one embodiment. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

In some instances, "PDC" may be used as an abbreviation for 1,2-dichloropropane, "TCP" may be used as an abbreviation for 1,2,3-trichloropropane and "TCPE" may be used as an abbreviation for 1,1,2,3-tetrachloropropene. The terms "cracking" and "dehydrochlorination" are used interchangeably to refer to the same type of reaction, i.e., one resulting in the creation of a double bond typically via the removal of a hydrogen and a chlorine atom from adjacent carbon atoms in chlorinated hydrocarbon reagents.

The present invention provides efficient processes for the production of chlorinated propenes. The present processes comprise conducting successive free radical chlorination and dehydrochlorination steps on one or more chlorinated propanes comprising PDC using known free radical catalysts. The use of PDC, a byproduct in many chlorohydrin processes, as a starting material is economically more attractive than disposing of it via incineration, as may be done in connection with some conventional chlorohydrin processes.

The present process is further advantageous since a saleable product can be reached in fewer steps, resulting in lower capital costs as compared to conventional processes. More specifically, the fact that the present processes are conducted in the liquid phase, using free radical chlorination, is advantageous compared to conventional methods for producing chlorinated propenes using gas-phase thermal chlorination reactions because the production utility cost is lower for a process comprising liquid phase reactions, where evaporation of reactants is not required. In addition, the lower reaction temperatures used in the present liquid phase reactions tend to result in lower fouling rates than the higher temperatures used in connection with gas phase reactions. Higher fouling rates, in turn, tend to limit reactor lifetime and can lead to undesirable byproduct formation.

The present processes, in some embodiments, may also provide a reduction of caustic cracking steps as compared to conventional processes, and so, anhydrous HCl can be recovered. Anhydrous HCl is of greater value than the sodium chloride that would be produced as byproduct(s) if conventional caustic cracking steps were utilized. The present process thus results in the production of a by-product that may either be sold or used as a feedstock for other processes, e.g., ethylene oxyhalogenation to produce ethylene dichloride.

The present process can make use of one or more chlorinated alkanes to produce the desired chlorinated propenes. Desirably, the one or more chlorinated alkanes comprise 1,2-dichloropropane, which may be available at low cost due to its production as a by-product in many chlorohydrin processes. The process feedstock may also comprise trichloropropane, or other chlorinated alkanes, if desired. And, the one or more chlorinated alkanes may be generated within or upstream of the process, if desired, e.g., as a byproduct in a chlorohydrin process, or by any other methods known to those of ordinary skill in the art.

Any chlorinated propene may be produced using the present method, although those with 3-5 chlorine atoms are more commercially sought after, and production of the same may thus be preferred in some embodiments. In some embodiments, the process may be used in the production of 1,1,2,3-tetrachloropropene, which is highly sought after as a feedstock for refrigerants, polymers, biocides, etc.

Known free radical catalysts or initiators are desirably used to enhance the present process. Such catalysts may typically comprise one or more chlorine, peroxide or azo-(R—N=N—R') groups and/or exhibit reactor phase mobility/activity. As used herein, the phrase "reactor phase mobility/activity" means that a substantial amount of the catalyst or initiator is available for generating free radicals of sufficient energy which can initiate and propagate effective turnover of the product, the chlorinated and/or fluorinated propene(s), within the design limitations of the reactor.

Furthermore, the catalyst/initiator should have sufficient homolytic dissociation energies such that the theoretical maximum of free radicals is generated from a given initiator under the temperature/residence time of the process. It is especially useful to use free radical initiators at concentrations where free radical chlorination of incipient radicals is prevented due to low concentration or reactivity. Surprisingly, the utilization of the same, does not result in an increase in the production of impurities by the process, but does provide selectivities to the chlorinated propenes of at least 50%, or up to 60%, up to 70%, and in some embodiments, up to 80% or even higher.

Such free radical initiators are well known to those skilled in the art and have been reviewed, e.g., in "Aspects of some initiation and propagation processes," Bamford, Clement H. Univ. Liverpool, Liverpool, UK., Pure and Applied Chemistry, (1967), 15(3-4),333-48 and Sheppard, C. S.; Mageli, O. L. "Peroxides and peroxy compounds, organic," Kirk-Othmer Encycl. Chem. Technol., 3rd Ed. (1982), 17, 27-90.

Taking the above into consideration, examples of suitable catalysts/initiators comprising chlorine include, but are not limited to carbon tetrachloride, hexachloroacetone, chloroform, hexachloroethane, phosgene, thionyl chloride, sulfuryl chloride, trichloromethylbenzene, perchlorinated alkylaryl functional groups, or organic and inorganic hypochlorites, including hypochlorous acid, and t-butylhypochlorite, methylhypochlorite, chlorinated amines (chloramine) and chlorinated amides or sulfonamides such as chloroamine-T®, and the like. Examples of suitable catalysts/initiators comprising one or more peroxide groups include hydrogen peroxide, hypochlorous acid, aliphatic and aromatic peroxides or hydroperoxides, including di-t-butyl peroxide, benzoyl peroxide, cumyl peroxide and the like. Diperoxides offer an advantage of not being able to propagate competitive processes (e.g., the free radical chlorination of PDC to TCP (and its isomers) and tetrachloropropanes). In addition, compounds, such as azobisisobutyronitrile (AIBN) or 1,1'-azobis (cyclohexanecarbonitrile (ABCN), may have utility in effecting the chlorination of PDC to trichloropropanes and tetrachloropropanes under the conditions of this invention. Combinations of any of these may also be utilized.

The process or reactor zone may be subjected to pulse laser or continuous UV/visible light sources at a wavelength suitable for inducing photolysis of the free radical catalyst/initiator, as taught by Breslow, R. in *Organic Reaction Mechanisms* W. A. Benjamin Pub, New York p 223-224. Wavelengths from 300 to 700 nm of the light source are sufficient to dissociate commercially available radical initiators. Such light sources include, e.g., Hanovia UV discharge lamps, sunlamps or even pulsed laser beams of appropriate wavelength or energy which are configured to irradiate the reactor chamber. Alternatively, chloropropyl radicals may be generated from microwave discharge into a bromochloromethane feedsource introduced to the reactor as taught by Bailleux et al., in Journal of Molecular Spectroscopy, 2005, vol. 229, pp. 140-144.

In some embodiments, the dehydrochlorination steps of the present process may be carried out in the presence of a catalyst so that the reaction rate is enhanced and also use of liquid caustic is reduced, or even eliminated, from the process. Such embodiments are further advantageous in that anhydrous HCl is produced, which is a higher value byproduct than aqueous HCl. If the use of catalysts is desired, suitable dehydrochlorination catalysts include, but are not limited to, ferric chloride ($FeCl_3$) as a substitute to caustic.

In other embodiments, the dehydrochlorination steps of the present process may be conducted in the presence of a liquid caustic. Although vapor phase dehydrohalogenations advantageously result in the formation of a higher value byproduct than liquid phase dehydrohalogenations, liquid phase dehydrohalogenation reactions can provide cost savings since evaporation of reactants is not required. The lower reaction temperatures used in liquid phase reactions may also result in lower fouling rates than the higher temperatures used in connection with gas phase reactions, and so reactor lifetimes may also be optimized when at least one liquid phase dehydrochlorination is utilized.

Many chemical bases are known in the art to be useful for this purpose, and any of these can be used. For example, suitable bases include, but are not limited to, alkali metal hydroxides, such as sodium hydroxide, potassium hydroxide, calcium hydroxide; alkali metal carbonates such as sodium carbonate; lithium, rubidium, and cesium or combinations of these. Phase transfer catalysts such as quaternary ammonium and quaternary phosphonium salts can also be added to improve the dehydrochlorination reaction rate with these chemical bases.

Any or all of the catalysts utilized in the process can be provided either in bulk or in connection with a substrate, such as activated carbon, graphite, silica, alumina, zeolites, fluorinated graphite and fluorinated alumina. Whatever the desired catalyst (if any), or format thereof, those of ordinary skill in the art are well aware of methods of determining the appropriate format and method of introduction thereof. For example, many catalysts are typically introduced into the reactor zone as a separate feed, or in solution with other reactants.

The amount of any free radical chlorination and/or dehydrochlorination catalyst utilized will depend upon the particular catalyst chosen as well as the other reaction conditions. Generally speaking, in those embodiments of the invention wherein the utilization of a catalyst is desired, enough of the catalyst should be utilized to provide some improvement to reaction process conditions (e.g., a reduction in required temperature) or realized products, but yet not be more than will provide any additional benefit, if only for reasons of economic practicality.

For purposes of illustration only then, it is expected that useful concentrations of the free radical initiator will range from 0.001% to 20% by weight, or from 0.01% to 10%, or from 0.1% to 5 wt. %. If a dehydrochlorination catalyst is utilized for one or more dechyrdochlorination steps, useful concentrations may range from 0.01 wt. % to 5 wt. %, or from 0.05 wt. % to 2 wt. % at temperatures of 70° C. to 200° C. If a chemical base is utilized for one or more dehydrochlorinations, useful concentrations of these will range from 0.01 to 20 grmole/L, or from 0.1 grmole/L to 15 grmole/L, or from 1 grmole/L to 10 grmole/L, inclusive of all subranges therebetween. Relative concentrations of each catalyst/base are given relative to the feed, e.g., 1,2-dichloropropane alone or in combination with 1,2,3-trichloropropane.

The chlorination steps of the process may be carried out using any chlorination agent, and several of these are known in the art. For example, suitable chlorination agents include, but are not limited to chlorine, and/or sulfuryl chloride ($SO_2Cl_2$). Combinations of chlorinating agents may also be used. Either or both $Cl_2$ and sulfuryl chloride may be particularly effective when aided by the use of the aforementioned ionic chlorination catalysts.

In additional embodiments, one or more reaction conditions of the process may be optimized, in order to provide even further advantages, i.e., improvements in selectivity, conversion or production of reaction by-products. In certain embodiments, multiple reaction conditions are optimized and even further improvements in selectivity, conversion and production of reaction by-products produced can be seen.

Reaction conditions of the process that may be optimized include any reaction condition conveniently adjusted, e.g., that may be adjusted via utilization of equipment and/or materials already present in the manufacturing footprint, or that may be obtained at low resource cost. Examples of such conditions may include, but are not limited to, adjustments to temperature, pressure, flow rates, molar ratios of reactants, mechanical mixing, etc.

That being said, the particular conditions employed at each step described herein are not critical, and are readily determined by those of ordinary skill in the art. What is important is that PDC is utilized as a starting material, and/or at least one chlorination step is conducted in the liquid phase and/or that provisions are made for the recovery of anhydrous HCl. The order of the following reaction steps is unimportant, and those of ordinary skill in the art will readily be able to determine suitable equipment for each step, as well as the particular conditions at which the halogen exchange, chlorination, dehydrohalogenation, separation, drying, and isomerization steps may be conducted. However, in those embodiments wherein dehydrochlorination occurs prior to chlorination, recovery of as much, or any HCl, may not be possible, and the yield or selectivity of the reaction may be somewhat less as compared to those embodiments wherein a chlorination step is carried out prior to one or more dehydrochlorinations.

In the present process, a feedstream comprising PDC, either alone, or in some embodiments, in combination with other alkanes such as 1,2,3-trichloropropane, is converted to TCPE using at least one chlorination step conducted in the presence of a free radical catalyst/initiator.

Figure 1:
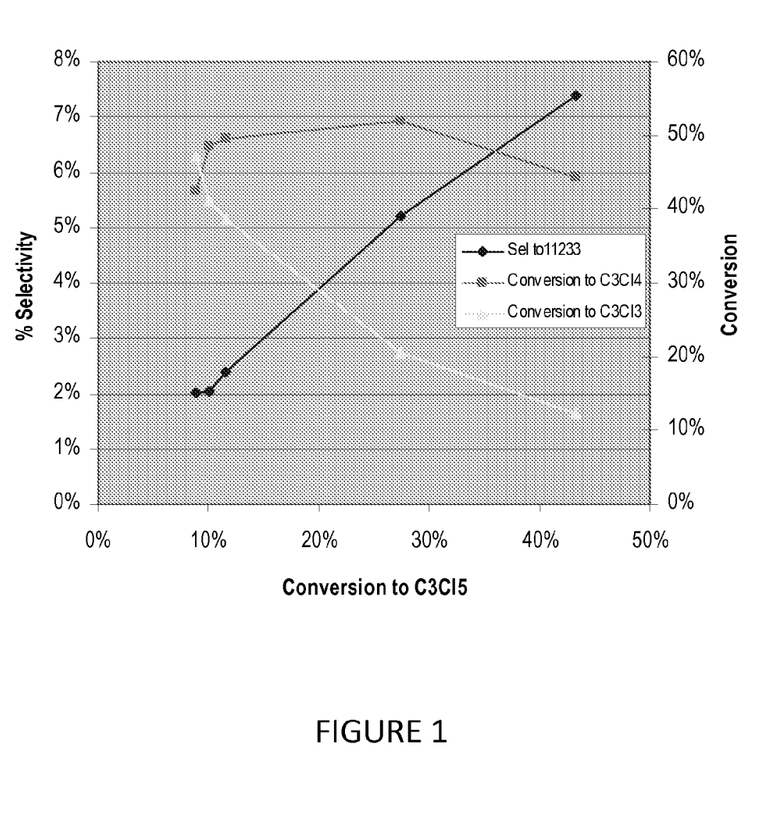
FIG. 1 shows a graph of the selectivity to 1,1,2,3,3-pentachloropropane isomer (11233), $C_3H_4Cl_4$ ($C_3Cl_4$) isomers, and $C_3H_5Cl_3$ isomers ($C_3Cl_3$) as a function of total conversion to pentachloropropane isomers under complete (>99%) PDC conversion.

In one exemplary embodiment, PDC is fed to a liquid phase chlorination reactor, e.g., such as a batch or continuous stirred tank autoclave reactor with an internal cooling coil. A shell and multitube exchanger followed by vapor liquid disengagement tank or vessel can also be used. Suitable reaction conditions include, e.g., a temperature of from 30° C. to 150° C., a pressure of from 100 kPa to 1000 kPa. Desirably, PDC conversion is controlled so that the production of hexachloropropanes and 1,1,2,3,3-pentachloropropane production is minimized As shown in FIG. 1, if PDC conversion to pentachlorinated propanes is maintained at less than or equal to 30%, selectivity to the less desirable pentachlorinated propane isomer (1,1,2,3,3-pentachloropropane) is less than 5%.

The process may be carried out neat, i.e., in the absence of solvent, or, one or more solvents may be provided to the chlorination reactor, and may be provided as feedstock, or, recycled from one or more separation columns operably disposed to receive streams from the chlorination reactor. For example, monochloropropene intermediates may be recycled back to the chlorination reactor from one separation column, tri- and tetrachloropropane intermediates may be recycled from another separation column and/or the chlorination reactor may be provided with a feedstock of any appropriate solvent for chlorination reactions, such as, e.g., carbon tetrachloride, sulfuryl chloride, 1,1,2,3,3-pentachloropropane, 1,1,2,2,3,3-hexachloropropane, other hexachloropropane isomers, or other suitable aqueous or alcohol based solvents, or a combination of these.

The overhead vapor from the chlorination reactor, is cooled, condensed and fed to a first separation column. This column is operated at conditions effective to provide anhydrous HCl to an overhead line thereof and chlorine through a bottom recycle line.

More particularly, the top temperature of such a column can typically be set below 0° C. or more preferably, can be set at a temperature of from −70° C. to −10° C. The bottom temperature of this column is desirably set at from 10° C. to 150° C., or from 30° C. to 100° C., with the exact temperature dependent to some degree on the bottom mixture composition. The pressure of this column is desirably set above 200 kPa or preferably, from 500 kPA to 2000 kPa, or more preferably from 500 kPa to 1000 kPa. The bottom stream of a column operated at such conditions would be expected to contain excess chlorine, unreacted PDC and monochloropropene intermediates, while the overhead stream would be expected to comprise anhydrous HCl.

The liquid product stream from the chlorination reactor may be fed to a second separation column operated at conditions effective to separate the tri- and tetra-chlorinated propanes from the pentachlorinated propanes. The overhead stream from this separation column, comprising tri- and tetrachlorinated propanes, may be recycled back to the chlorination reactor for further conversion/chlorination, while the bottom stream, expected to comprise pentachloropropanes and heavier by-products, such as isomers of hexachloropropanes, may be provided to a further separation column.

This third separation column separates the desirable pentachloropropanes, i.e., 1,1,2,2,3-pentachloropropane, 1,1,1,2,3-pentachloropropane, and 1,1,1,2,2-pentachloropropane, from the less desirable 1,1,2,3,3-pentachloropropane and heavier components, which are purged as a bottom stream.

The overhead stream comprising 1,1,2,2,3-pentachloropropane, 1,1,1,2,3-pentachloropropane, and 1,1,1,2,2-pentachloropropane is then provided to a reactor where it is dehydrochlorinated to provide 2,3,3,3-tetrachloropropene and 1,1,2,3-tetrachloropropene. More specifically, dehydrochlorination reactor may typically be a batch or a continuous stirred tank reactor. The mixing can be done, e.g., by mechanical or jet mixing of feed streams. Those of ordinary skill in the art are readily able to determine the appropriate conditions at which to run a dehydrochlorination reactor in order to conduct the aforementioned dehydrochlorination.

The reaction stream from the dehydrochlorination reactor may optionally be provided to a drying column, and the dried stream therefrom provided to a further reactor to isomerize the 2,3,3,3-tetrachloropropene to 1,1,2,3-tetrachloropropene under the appropriate conditions. For example, catalysts may be utilized to assist in the isomerization, in which case, suitable catalysts include, but are not limited to (i) siliceous granules having a polar surface including kaolinite, bentonite, and attapulgite; (ii) other mineral salts of silica such as saponite, quartz, (iii) siliceous non-mineral substance such as silica gel, fumed silica, and glass, or combinations of any of these. Suitable conditions for drying columns for such reaction streams are also known to those of ordinary skill in the art, as evidenced by U.S. Pat. No. 3,926,758.

Figure 2:
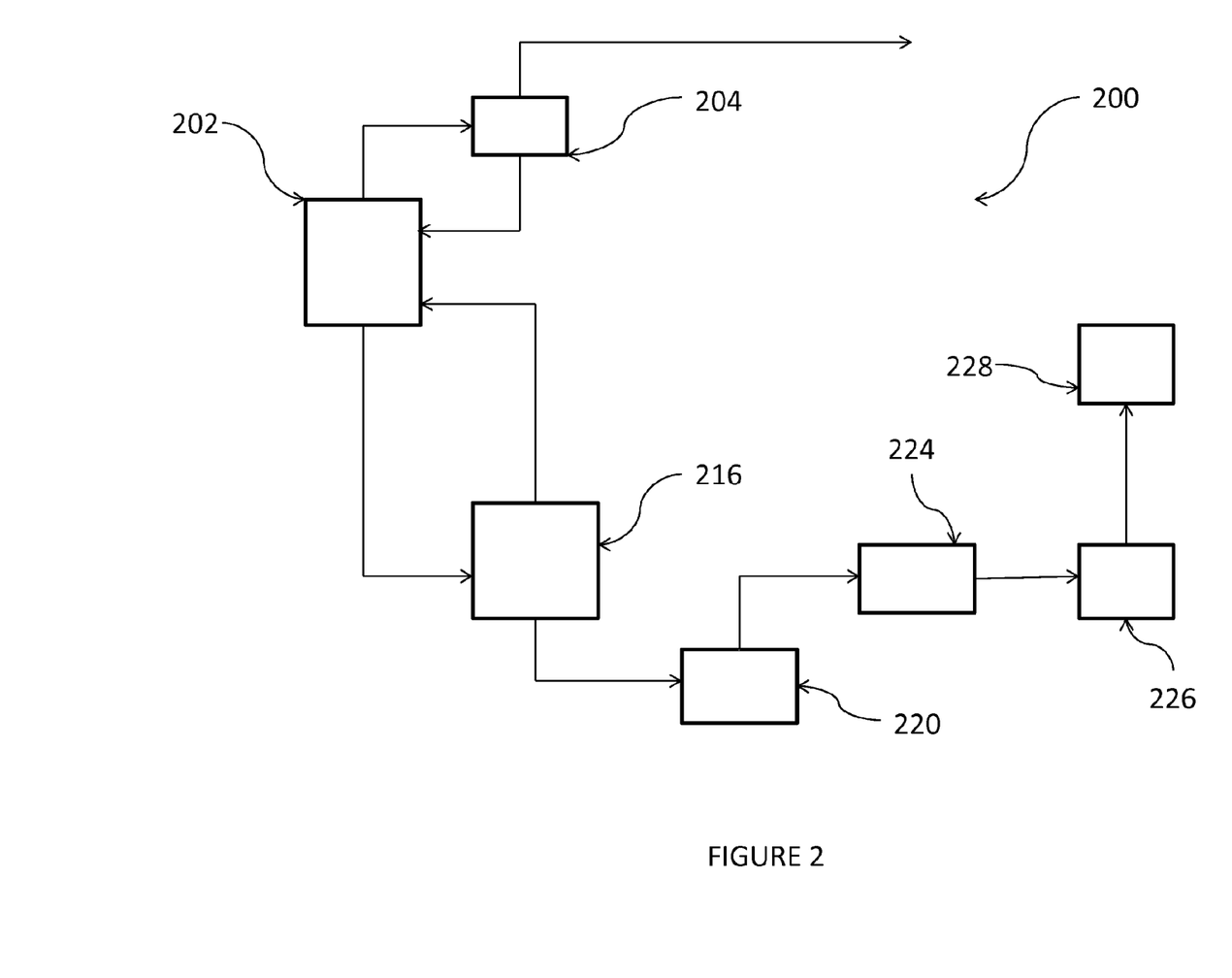
FIG. 2 shows a schematic representation of a process according to one embodiment.

A schematic illustration of such a process is shown in FIG. 2. As shown in FIG. 2, process 200 would make use of chlorination reactor 202, separation columns 204, 216 and 220, dehydrochlorination reactor 224, dryer 226 and isomerization reactor 228. In operation, 1,2-dichloropropane (alone or in combination with trichloropropane) the desired chlorination agent (e.g., chlorine, $SO_2Cl_2$, or combinations of these) and one or more free radical catalysts such as dibenzoyl peroxide and/or AIBN are fed, or otherwise provided, to chlorination reactor 202, which may be operated at any set of conditions operable to provide for the chlorination of PDC to tri-, tetra- and pentachlorinated propanes. In some embodiments, chlorination reactor 202 may be operated at conditions effective to provide a selectivity to 1,1,2,3,3-pentachloropropane of less than 5%, as described above.

The overhead vapor stream of reactor 202 is cooled, condensed and fed to separation column 204, which may desirably be a distillation column. Separation column 204 is operated at conditions effective to provide anhydrous HCl through an overhead line and chlorine, PDC and monochloropropene intermediates back to chlorination reactor 202.

The bottom stream of reactor 202 is fed to separation column 216, which is operated at conditions effective to separate the tri- and tetrachlorinated propanes from the pentachlorinated propanes. The tri- and tetra chlorinated propanes are fed back to chlorination reactor 202 for further conversion/chlorination, while the bottom stream from separation column 216 is fed to separation column 220.

Separation column 220 separates the bottom stream from separation column 216 into an overhead stream comprising the desirable pentachloropropane isomers (1,1,1,2,2-pentachloropropane, 1,1,2,2,3-pentachloropropane and 1,1,1,2,3-pentachloropropane) and a bottom stream comprising the less desirable 1,1,2,3,3-pentachloropropane, hexachloropropane and heavier by-products. The overhead stream is fed to dehydrochlorination reactor 224, while the bottoms stream is appropriately disposed of [not shown].

Within dehydrochlorination reactor 224, the desirable pentachloropropane isomers are dehydrochlorinated, or cracked, using sodium hydroxide to provide 2,3,3,3-tetrachloroprene and 1,1,2,3-tetrachlropropene, and the conditions to do so are either well-known, or readily determined, by those of ordinary skill in the art. Generally speaking, dehydrochlorination reactor 224 may be charged with caustic soda at 50% aqueous solution at concentration of from 0.01 grmole/L to 100 grmole/L, or from 0.1 grmole/L to 10 grmole/L, and operated at pressures of from ambient to 400 kPA and temperature of from 40° C. to 150° C., or from 60° C. to 120° C. and at residence times of less than 3 hours. The product stream of dehydrochlorination reactor 224 is fed to drying unit 226, and then to isomerizing reactor 228, wherein the dried 2,3,3,3-tetrachloropropene is isomerized to TCPE using catalyst as described in, e.g., U.S. Pat. No. 3,926,758.

Figure 3:
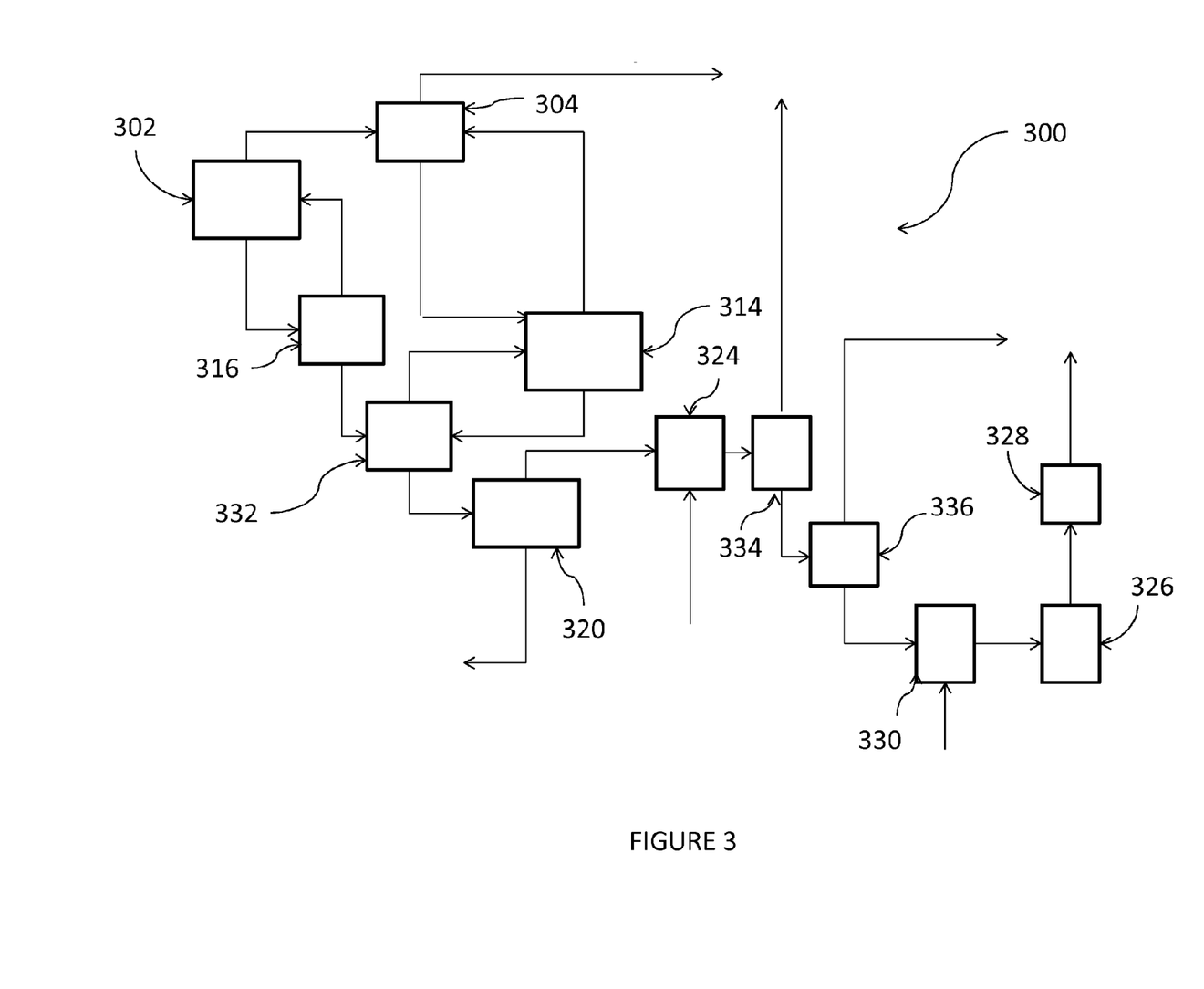
FIG. 3 shows a schematic representation of a process according to a further embodiment.

A schematic illustration of another embodiment of the process is shown in FIG. 3. As shown in FIG. 3, process 300 could operate on equipment comprising chlorination reactor(s) 302 and 314, separation columns 304, 316, 320, 332, 334 and 336, dehydrochlorination reactors 324 and 330, dryer 326 and isomerization reactor 328. The process as shown in FIG. 3 thus makes use of one additional chlorination reactor 314 and cracking reactor 330 as compared to process 200, yet operates in much the same way.

In operation, 1,2-dichloropropane (alone or in combination with trichloropropane) and the desired chlorination agent (e.g., chlorine), and initiators such as AIBN and/or dibenzoyl peroxide, or combinations of these) are fed to chlorination reactor 302, which may be operated at any set of conditions operable to provide for the chlorination of PDC to tri-, tetra and pentachlorinated propanes.

The overhead stream of reactor 302 is fed to separation column 304, which may desirably be a distillation or fractionation column. Separation column 304 is operated at conditions effective to provide anhydrous HCl through an overhead line and chlorine to second chlorination reactor 314. Second chlorination reactor 314 is used to more selectively convert 1,1,2,3-tetrachloropropane to the desired pentachloropropane isomers, i.e., 1,1,1,2,3-pentachloropropane and 1,1,2,2,3-pentachloropropane, while minimizing the formation of 1,1,2,3,3-pentachloropropane. The valuable byproduct HCl evolved in the second chlorination reactor 314 is gaseous under the conditions used. This byproduct and excess $Cl_2$ in the overhead stream are fed back to column 304 for recovery.

The operating conditions of separation column 316 can be adjusted so that the overhead stream contains more of the trichloropropane and desirable tetrachloropropane isomers than the less desirable 1,1,2,3-tetrachloropropane isomer(s) with boiling points lower than that of 1,1,2,3-tetrachloropropane (178° C.) such as 1,1,1,2-tetrachloropropane (Bp 150° C.), 1,1,2,2-tetrachloropropane (Bp 155° C.), and 1,2,2,3-tetrachloropropane (Bp 164° C.). (see C. L. Yaws, "Thermophysical Properties of Chemicals and Hydrocarbons," 2008). The 1,1,2,3-tetrachloropropane and heavier products and byproducts are fed to separation column 332.

Separation column 332 provides 1,1,2,3-tetrachloropropane (see, e.g., U.S. Pat. No. 3,382,195) to chlorination reactor 314, and the resulting pentachloropropanes fed back to separation column 332. The bottom stream from separation column 332, comprising pentachloropropane and heavier byproducts, is fed to separation column 320, which separates and purges the heavy byproducts therefrom.

The desired 1,1,1,2,3-pentachloropropane isomer is fed to dehydrochlorination reactor 324 and catalytically cracked, e.g., using $FeCl_3$, to produce TCPE and HCl, allowing recovery of HCl through an overhead line of separation column 334. TCPE can then be removed from an overhead line of separation column 336, and the rest of the pentachloropropane intermediates can be caustic cracked in dehydrochlorination reactor 330, using e.g., sodium hydroxide. As in the process described in connection with FIG. 2, the 2333e and TCPE product from dehydrochlorination reactor 330 is dried in dryer 326 and 2333e is isomerized to TCPE in isomerization reactor 328.

Figure 4:
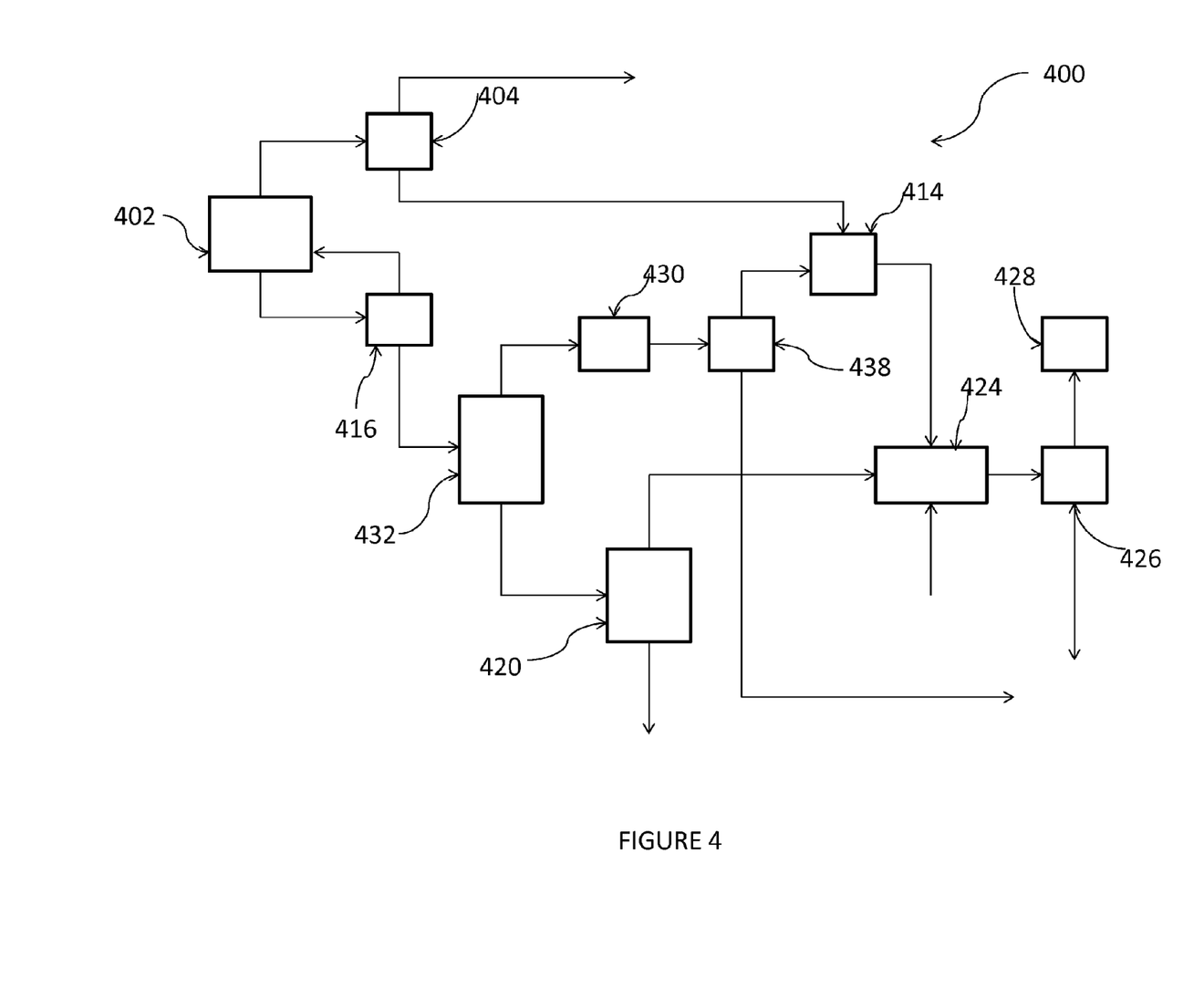
FIG. 4 shows a schematic representation of a process according to a further embodiment.

Yet another embodiment of the process is shown in FIG. 4. More particularly, the process as shown in FIG. 4 operates similarly to process 300 shown in FIG. 3, with the exception that 1,1,2,3-tetrachloropropane is not recycled back to the first chlorination reactor, but recovered in the overhead stream of separation column 432. And so, in process 400, the 1,1,2,3-tetrachloropropane is not further chlorinated, but it is caustic cracked in dehydrochlorination reactor 430 to provide trichloropropenes such as 1,2,3-trichloropropene. This product stream is then fed to dryer 438 and then chlorination reactor 414 to produce pentachloropropanes (with high selectivity to 1,1,2,2,3-pentachloropropane).

The product stream from chlorination reactor 414 is provided to dehydrochlorination reactor 424 where it is combined with the overhead stream from separation column 420, containing other desirable pentachloropropane intermediates, and further dehydrochlorinated.

The rest of process 400 proceeds as processes 200 and 300, i.e., with the organic layer from dehydrochlorination reactor 424 being dried in dryer 426 and the isomer 2333e being converted to TCPE in isomerization reactor 428. The process shown in FIG. 4 is expected to exhibit better yield to TCPE than processes 300 since this process further minimizes 11233 production. However, less anhydrous HCl is expected to be recovered due to the use of a liquid phase dehydrochlorination within both dehydrochlorination reactors 424 and 430.

Figure 5:
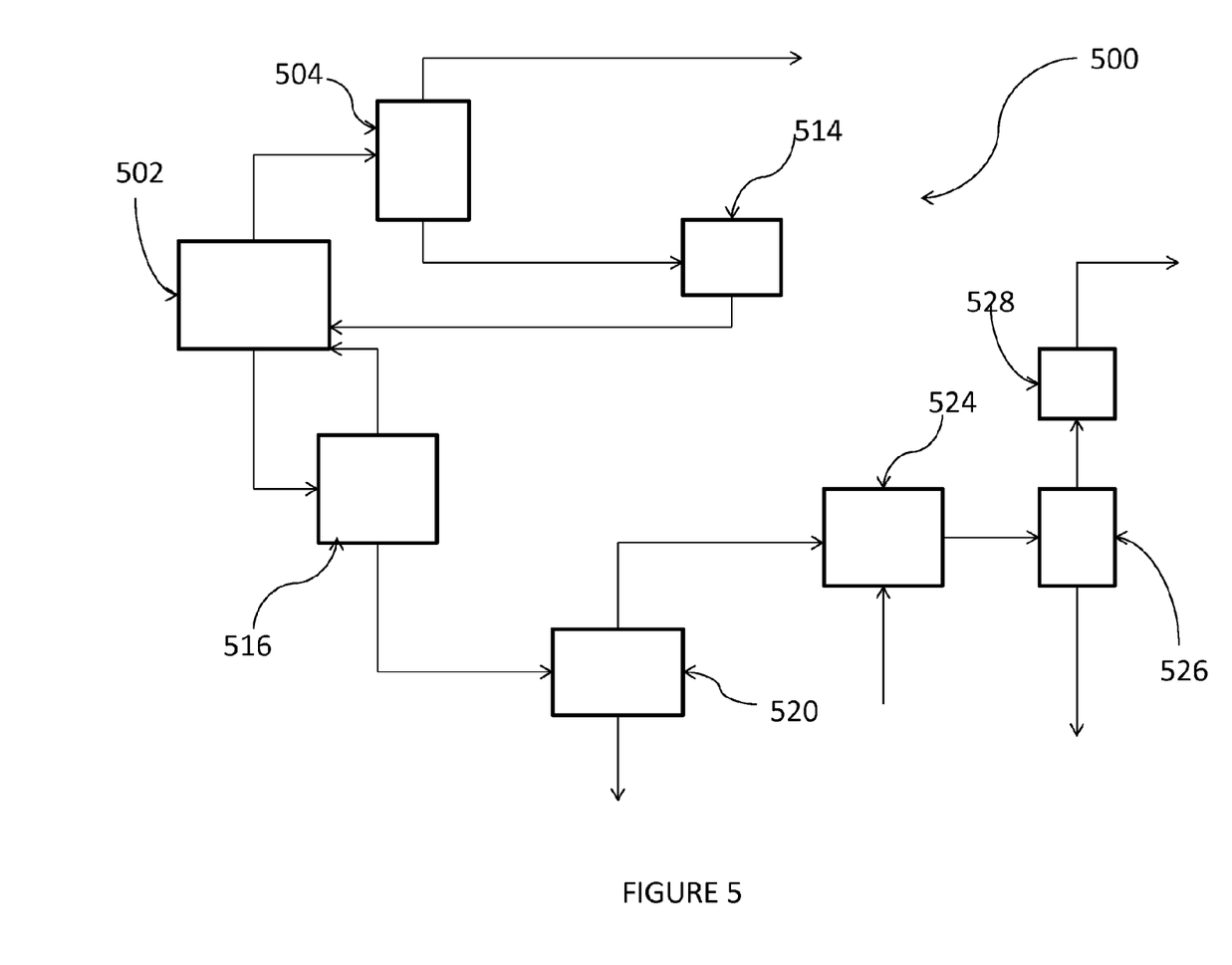
FIG. 5 shows a schematic representation of a process according to a further embodiment.

Yet another embodiment of the process is shown in FIG. 5. In process 500, sulfuryl chloride ($SO_2Cl_2$) may be used in place of chlorine in chlorination reactor 502. The vapor overhead of chlorination reactor 502 will thus contain $SO_2$, HCl byproducts and some monochloropropene intermediates. After removing these via an overhead stream of separation column 504, the bottom stream from separation column 504, comprising mostly $SO_2$, is fed to second chlorination reactor 514 and chlorinated to produce $SO_2Cl_2$, which may then be recycled back to chlorination reactor 502. The use of $SO_2Cl_2$ is beneficial since $SO_2Cl_2$ is more miscible with PDC with or without TCP in chlorination reactor 502, thus possibly providing better process yield and productivity. Process 500 otherwise proceeds identically to process 200, shown in FIG. 2.

Figure 6:
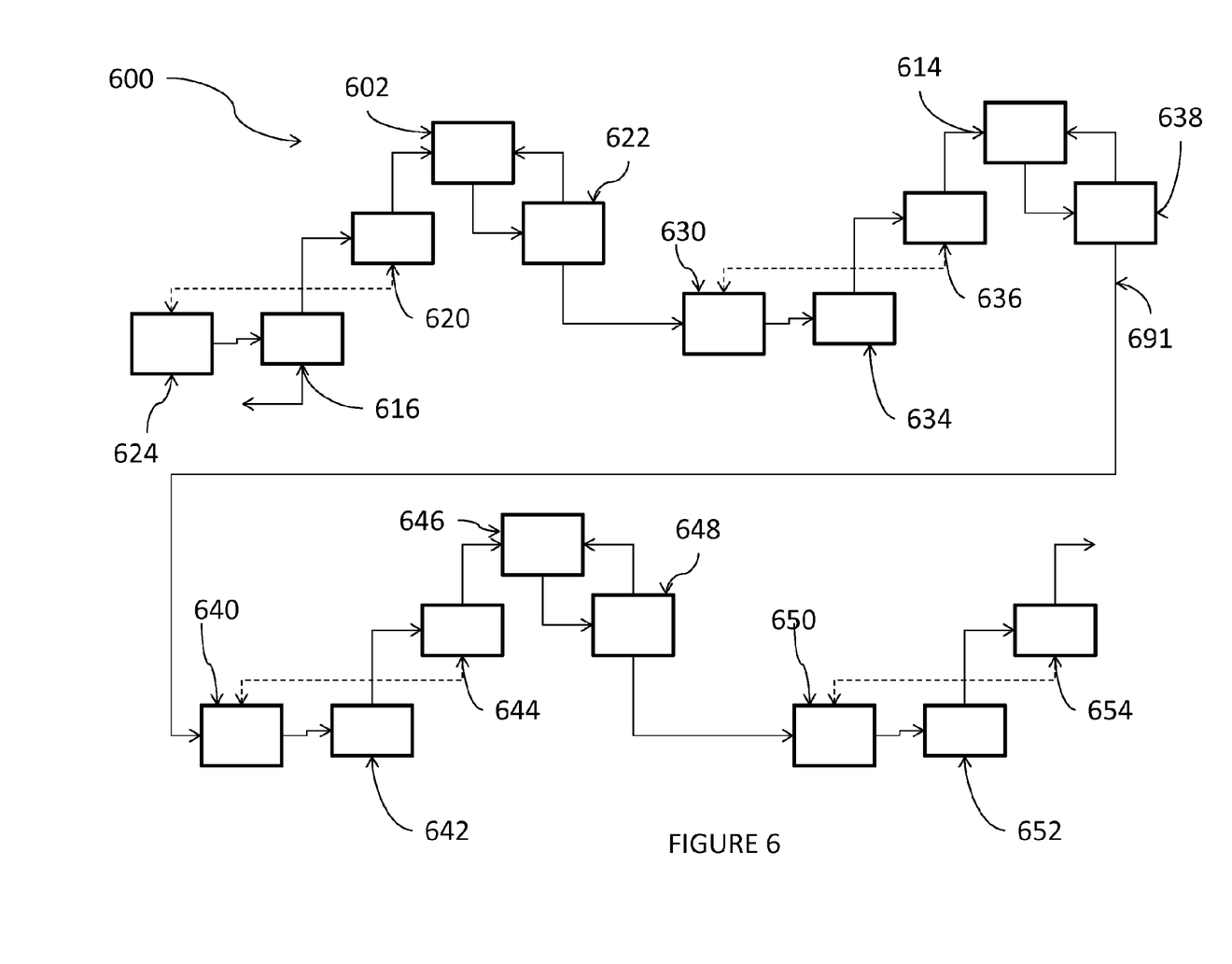
FIG. 6 shows a schematic representation of a process according to a further embodiment.

Yet another embodiment of the present process is shown in FIG. 6. As shown in FIG. 6, process 600 would operate on equipment comprising chlorination reactor(s) 602, 614 and 646, dehydrochlorination reactors 624, 630, 640 and 650, and separation columns 616, 620, 622, 634, 636, 638, 642, 644, 648, 652 and 654. Process 600 illustrates one embodiment wherein a dehydrochlorination step occurs prior to a chlorination step.

In process 600, PDC is dehydrochlorinated in dehydrochlorination reactor 624, to a mixture of cis/trans-1-chloropropene, 2-chloropropene, and allyl chloride using caustic solution at a temperature of from 50° C. to 100° C., a residence time of less than two hours, and at a pressure ranging from 100 kPa to 200 kPa. The product stream, comprising monochloropropenes, water, sodium chloride, excess caustic and unreacted PDC, is fed to separation column 616. The monochloropropenes and PDC are recovered in the overhead stream, while sodium chloride, caustic, and aqueous solution is purged as the bottom stream from separation 616.

The overhead stream from separation column 616 is fed to separation column 620 which provides unreacted PDC as a bottom stream to dehydrochlorination reactor 624. The overhead stream from separation column 620, comprising monochloropropene intermediates, is fed to the chlorination reactor 602, along with a fresh chlorinating agent, such as $Cl_2$ (not shown). Chlorination reactor 602, which may be, e.g., a continuous stirred tank reactor, is operated at temperatures of from 30° C. to 100° C. and at a pressure of 100 kPa for a residence time of less than an hour. The reaction product, comprising trichloropropane isomers, is taken as a bottom stream from chlorination reactor 602 and fed to separation column 622.

Separation column 622 recovers unreacted monochloropropenes from the bottom stream of chlorination reactor 602 and recycles them back to chlorination reactor 602 via an overhead stream, while the bottom stream from separation column 622, comprising a mixture of trichloropropane isomers and trichloropropane isomers is fed to dehydrochlorination reactor 630.

Dehydrochlorination reactor 630 is operated at conditions similar to those used for dehydrochlorination reactor 624, and the organic product is fed to separation column 634 wherein it is separated into overhead stream, comprising unconverted trichloropropanes, and bottom stream, comprising NaCl, water, and excess NaOH. The overhead stream from separation column 634 is fed to separation column 636, while the bottom stream is disposed of.

Separation column 636 separates unconverted trichloropropanes from dichloropropene intermediate products and recycles the unconverted trichloropropanes to dehydrochlorination reactor 630. The dichloropropene intermediates, i.e., 1,1-dichloropropene, 1,2-dichloropropene, and 2,3-dichloropropene, are fed to chlorination reactor 614.

Chlorination reactor 614 is operated at similar conditions to that of chlorination reactor 602, with the exception that a mixture of tetrachloropropanes may be used as solvent in this reactor. In chlorination reactor 614, the dichloropropene is converted to a mixture of 1,1,1,2-tetrachloropropane, 1,1,2,2-tetrachloropropane, and 1,2,2,3-tetrachloropropane. The product of chlorination reactor 614 is fed to separation column 638.

Separation column 638 may desirably be operated at a pressure of less than 100 kPa. Unreacted dichloropropenes from separation column 638 are recycled back to chlorination reactor 614. The tetrachloropropane intermediates in the bottom stream of separation column 638 are then fed to dehydrochlorination reactor 640. Dehydrochlorination reactor 640 is operated at similar conditions to those used in dehydrochlorination reactors 624 and 630, and converts the tetrachloropropanes to trichloropropenes, i.e., 3,3,3-trichloropropene, 1,1,2-trichloropropene, and 1,2,3-trichloropropene.

The product stream from dehydrochlorination reactor 640, comprising unreacted tetrachloropropenes and trichloropropene and aqueous byproducts, is fed to separation column 642 to recover the unreacted tri- and tetrachloropropenes and provide them to separation column 644. The bottom stream from separation column 644 is recycled back to dehydrochlorination reactor 640, while the overhead stream, comprising trichloropropenes is provided to chlorination reactor 646.

Chlorination reactor 646 operates under similar conditions as those used in chlorination reactors 602 and 614, with the exception that the product pentachloropropane acts as the diluent within chlorination reactor 646. The product stream from chlorination reactor 646, comprising 1,1,1,2,3-pentachloropropane, 1,1,1,2,2-pentachloropropane, and 1,1,2,2,3-pentachlororopane, is removed as a bottom stream and provided to separation column 648, operated at <100 kPa to recover unreacted trichloropropene in the overhead stream, recycled to chlorination reactor 646, and tetrachloropropane isomers in the bottom stream. The bottom stream is then fed to dehydrochlorination reactor 650, which is operated under similar condition to that of dehydrochlorination reactors 624, 630 and 640 to produce 2,3,3,3-tetrachlropropane and TCPE.

The product stream from dehydrochlorination reactor 650 is provided to separation column 652, operated under vacuum, wherein tetrachlropropenes and unreacted pentachloropropane are recovered as an overhead stream. The tetrachloropropenes are purified as overhead stream by separation column 654 operated at <40 kPa. The bottom stream from separation column 654, comprising unreacted pentachloropropane, is recycled back to dehydrochlorination reactor 650. The 2,3,3,3-tetrachloropropene is then isomerized to TCPE, according to methods known to those of ordinary skill in the art. (not shown in FIG. 6).

While this example requires many unit operations, it nonetheless establishes that TCPE can be produces from one or more chlorinated alkanes comprising PDC when dehydrochlorination is used as a first step, and wherein free radical initiators are used in subsequent chlorination steps.

The chlorinated and/or fluorinated propenes produced by the present process may typically be processed to provide further downstream products including hydrofluoroolefins, such as, for example, 1,3,3,3-tetrafluoroprop-1-ene (HFO-1234ze). Since the present invention provides an improved process for the production of chlorinated and/or fluorinated propenes, it is contemplated that the improvements provided will carry forward to provide improvements to these downstream processes and/or products. Improved methods for the production of hydrofluoroolefins, e.g., such as 2,3,3,3-tetrafluoroprop-1-ene (HFO-1234yf), are thus also provided herein.

The conversion of chlorinated and/or fluorinated propenes to provide hydrofluoroolefins may broadly comprise a single reaction or two or more reactions involving fluorination of a compound of the formula $C(X)_mCCl(Y)_n(C)(X)_m$ to at least one compound of the formula $CF_3CF=CHZ$, where each X, Y and Z is independently H, F, Cl, I or Br, and each m is independently 1, 2 or 3 and n is 0 or 1. A more specific example might involve a multi-step process wherein a feedstock of a chlorinated and/or fluorinated propene is fluorinated in a catalyzed, gas phase reaction to form a compound such as 1-chloro-3,3,3-trifluoropropene (1233zd). The 1-chloro-2,3,3,3-tetrafluoropropane is then dehydrochlorinated to 1,3,3,3-tetrafluoropropene via a catalyzed, gas phase reaction.

In the following examples, individual chloropropane isomers are identified by reference to the positions of the chlorine atoms, i.e., 112 indicates 1,1,2-trichloropropane, 1123 indicates 1,1,2,3-tetrachloropropane, 11223 indicates 1,1,2,2,3-pentachloropropane, and so on.

EXAMPLE I

In this example, liquid $SO_2Cl_2$ and PDC (1,2-dichloropropane) are mixed in a 100 ml flask heated in a water bath to maintain temperature 55° C. to 60° C. A reflux column is placed to return unreacted sulfuryl chloride and PDC, that are stripped by $SO_2$ and HCl byproducts, to the reaction flask.

Table 1 shows the product distribution, as determined by GC/MS, at various SO$_2$Cl$_2$ and/or AIBN initiator concentrations at near complete PDC conversions. As shown by both Table 1 and FIG. 1, this process, using high excess SO$_2$Cl$_2$ at 45% total conversion to pentachloropropane isomers, provides less than 8% molar selectivity to the less desirable pentachloropropane, 1,1,2,3,3-pentachloropropane (11233).

TABLE 1

| | SO2Cl2/PDC | | | | |
|---|---|---|---|---|---|
| | 3 | 3 | 5 | 5 | 6 |
| | | | AIBN/PDC | | |
| | 0 | 2 | 1 | 2 | 3 |
| PDC conversion | 98.5% | 100.0% | 100.0% | 100.0% | 100.0% |
| | | | Selectivity | | |
| 11223 | 3.3% | 3.7% | 5.0% | 11.8% | 19.4% |
| 11233 | 2.0% | 2.0% | 2.4% | 5.2% | 7.4% |
| 11122 | 1.3% | 1.7% | 2.5% | 6.3% | 10.7% |
| 11123 | 2.3% | 2.6% | 1.7% | 4.1% | 5.8% |
| 1122 | 13.2% | 17.8% | 19.4% | 21.2% | 23.9% |
| 1123 | 15.6% | 15.6% | 14.8% | 10.8% | 8.9% |
| 1223 | 10.1% | 11.8% | 12.3% | 12.9% | 9.7% |
| 1112 | 3.6% | 3.3% | 3.0% | 7.0% | 1.8% |

TABLE 1-continued

| | SO2Cl2/PDC | | | | |
|---|---|---|---|---|---|
| | 3 | 3 | 5 | 5 | 6 |
| | | | AIBN/PDC | | |
| | 0 | 2 | 1 | 2 | 3 |
| 112 | 8.9% | 6.5% | 6.7% | 4.6% | 0.2% |
| 122 | 18.0% | 19.7% | 19.7% | 9.4% | 6.2% |
| 123 | 20.3% | 14.8% | 12.2% | 6.6% | 5.8% |

EXAMPLE II

In this example, PDC (10 mL) is mixed in a 100 ml pressure reactor with 2,2'-azobis(2,4-dimethyl valeronitrile) (100 mg), dimethyl 2,2'-azobis(2-methylpropionate) (100 mg) or 1,1'-azobis(cyclohexane-1-carbonitrile) (100 mg) in carbon tetrachloride solvent (37.2 mL). The reactor is heated using a heating mantle to a temperature of ~70° C. A flow of gaseous Cl$_2$ in N$_2$ (30% v/v at STP) is passed through the mixture at a rate of about 100 sccm for the rest of the synthesis. A reactor pressure of ~130 psig is maintained during the experiment. $^1$H NMR spectroscopy is used to determine the product composition.

Table 2 shows the chlorinated product distribution after about 200 and 300 minutes of chlorine passing through solution. As also shown in Table 2 or FIG. 1, less than 8% molar selectivity to the less desirable byproduct 1,1,2,3,3-pentachloropropane (11233) is observed at all conversions.

TABLE 2

| | 2,2'-azobis(2,4-dimethyl valeronitrile) | | dimethyl 2,2'-azobis(2-methylpropionate) | | 1,1'-azobis(cyclohexane-1-carbonitrile) | |
|---|---|---|---|---|---|---|
| | Sample 1 | Sample 2 | Sample 1 | Sample 2 | Sample 1 | Sample 2 |
| Time | 196 | 304 | 192 | 252 | 199 | 335 |
| PDC Conversion | 80.97 | 86.00 | 96.69 | 97.27 | 99.91 | 100.00 |
| | | | Selectivity | | | |
| 11223 | 0.4% | 0.4% | 1.3% | 1.5% | 5.8% | 17.7% |
| 11233 | 0.2% | 0.2% | 0.6% | 0.6% | 2.4% | 5.3% |
| 11122 | 0.3% | 0.4% | 1.1% | 1.2% | 4.8% | 16.1% |
| 11123 | 0.0% | 0.0% | 0.6% | 0.5% | 1.5% | 3.4% |
| 1122 | 7.9% | 9.2% | 15.5% | 16.2% | 25.4% | 25.3% |
| 1123 | 5.4% | 6.5% | 9.6% | 9.9% | 12.6% | 5.6% |
| 1223 | 4.3% | 5.1% | 8.2% | 8.9% | 13.8% | 13.7% |
| 1112 | 1.9% | 2.2% | 3.1% | 3.1% | 3.3% | 1.2% |
| 112 | 20.9% | 19.2% | 13.3% | 12.5% | 3.7% | 0.1% |
| 123 | 17.5% | 17.0% | 11.1% | 10.7% | 3.6% | 0.0% |
| 122 | 41.3% | 39.7% | 35.7% | 34.7% | 22.6% | 6.4% |
| hex isomers | 0.0% | 0.0% | 0.0% | 0.1% | 0.6% | 5.3% |

EXAMPLE III

In this example, a 100 ml pressure reactor is charged with carbon tetrachloride (45 mL) and gaseous $Cl_2$ in $N_2$ (30% v/v at STP) is passed through the mixture while the pressure is held at about 150 psig until saturation is reached. The reactor is heated using a heating mantle to a temperature of ~70° C. and while the pressure is maintained at about 150 psig. Then, a solution containing PDC (10 mL) and free radical initiator dimethyl 2,2'-azobis(2-methylpropionate) (100 mg) is added. $^1H$ NMR spectroscopy is used to determine the product composition.

Table 3 shows the chlorinated C3 product distribution at various PDC conversions. As also shown in FIG. 1, less than 8% molar selectivity to the less desirable byproduct 1,1,2,3,3-pentachloropropane (11233) is observed at all conversions.

TABLE 3

|  | Sample 1 | Sample 2 |
| --- | --- | --- |
| Time | 17 | 32 |
| PDC Conversion | 98.9 | 99.6 |
|  | Selectivity | |
| 11223 | 2.6% | 3.7% |
| 11233 | 1.1% | 1.6% |
| 11122 | 2.2% | 3.3% |
| 11123 | 0.7% | 1.0% |
| 1122 | 20.1% | 23.0% |
| 1123 | 11.5% | 12.1% |
| 1223 | 10.9% | 12.3% |
| 1112 | 3.5% | 3.6% |
| 112 | 8.5% | 6.2% |
| 123 | 29.9% | 26.9% |
| 122 | 7.5% | 5.7% |
| hex isomers | 0.3% | 0.3% |

EXAMPLE IV

In this example, a 100 ml pressure reactor is charged with carbon tetrachloride (45 mL) and gaseous $Cl_2$ in $N_2$ (30% v/v at STP) is passed through the mixture while the pressure is held at about 150 psig. The reactor is heated using a heating mantle to a temperature of ~70° C. and while the pressure is maintained at about 150 psig. Then, a solution containing 1123-tetrachloropropane (3 mL), carbon tetrachloride (7 mL) and dimethyl 2,2'-azobis(2-methylpropionate) (100 mg) is added. $^1H$ NMR spectroscopy is used to determine the product composition.

Table 4 shows the chlorinated C3 product distribution at various conversions. Production of the undesirable 11233-pentachloropropane isomer is minimized when low conversions of 1123 are maintained.

TABLE 4

|  | Sample | | | | | | | |
| --- | --- | --- | --- | --- | --- | --- | --- | --- |
|  | 1 | 1 | 2 | 2 | 3 | 3 | 4 | 4 |
|  | Time (min) | | | | | | | |
|  | 6 | 6 | 18 | 18 | 63 | 63 | 125 | 125 |
|  | molar ratio | selectivity | molar ratio | selectivity | molar ratio | selectivity | molar ratio | selectivity |
| hex isomers | 0.03 | 1.10% | 0.02 | 0.93% | 0.11 | 4.18% | 0.16 | 6.28% |
| 11223 | 1.00 | 42.98% | 1.00 | 40.33% | 1.00 | 39.67% | 1.00 | 38.52% |
| 11233 | 0.84 | 36.02% | 0.94 | 38.05% | 0.97 | 38.42% | 0.98 | 37.67% |
| 11123 | 0.46 | 19.90% | 0.51 | 20.69% | 0.45 | 17.73% | 0.46 | 17.53% |
| 1123 | 24.97 |  | 18.08 |  | 6.02 |  | 4.17 |  |

EXAMPLE V

In this example, a 100 ml pressure reactor is charged with carbon tetrachloride (45 mL) and gaseous $Cl_2$ in $N_2$ (30% v/v at STP) is passed through the mixture while the pressure is held at about 150 psig. The reactor is heated using a heating mantle to a temperature of ~70° C. and while the pressure is maintained at about 150 psig. Then, a solution containing 1223-tetrachloropropane (3 mL), carbon tetrachloride (7 mL) and dimethyl 2,2'-azobis(2-methylpropionate) (100 mg) is added. $^1H$ NMR spectroscopy is used to determine the product composition.

Table 5 shows the chlorinated C3 product distribution at various conversions. Only the desirable 11223-pentachloropropane is formed with >90% selectivity with respect to hexachloropropane isomers over the range of conversions observed.

TABLE 4

| | Sample | | | | | |
|---|---|---|---|---|---|---|
| | 1 | 1 | 2 | 2 | 3 | 3 |
| | | | Time (min) | | | |
| | | | 2.00 | | 3.00 | |
| | 5 molar ratio | 5 selectivity | 21.00 molar ratio | 21 selectivity | 21.00 molar ratio | 60 selectivity |
| hex isomers | 0.01 | 1.38% | 0.02 | 2.15% | 0.03 | 3.29% |
| 11223 | 1.00 | 98.62% | 1.00 | 97.85% | 1.00 | 96.71% |
| 1223 | 16.73 | | 8.97 | | 4.94 | |

The invention claimed is:

1. A process for the production of chlorinated propenes from one or more chlorinated alkanes comprising 1,2-dichloropropane, comprising at least one liquid phase chlorination step conducted in the presence of a free radical initiator and at least one dehydrochlorination step, wherein the free radical initiator comprises an azo compound, UV light, or a combination of these.

2. The process of claim 1, wherein the one or more chlorinated alkanes further comprise 1,2,3-trichloropropane.

3. The process of claim 1 or 2, wherein the chlorination step produces a mixture of trichloropropane, tetrachloropropane, and pentachloropropane.

4. The process of claim 1, wherein the chlorination agent comprises chlorine or $SO_2Cl_2$, or combinations of these.

5. The process of claim 1, wherein the free radical initiator further comprises one or more peroxide compounds.

6. The process of claim 1, wherein the chlorinated propene comprises 1,1,2,3-tetrachloropropene.

7. The process of claim 1, wherein HCl is generated as a byproduct and recovered as anhydrous HCl.

8. The process of claim 1, further comprising the use of a solvent in the chlorination step, wherein the solvent comprises PDC, trichloropropane isomers, tetrachloropropane isomers, carbon tetrachloride or combinations of these.

9. The process of claim 1, wherein at least one chlorination step generates a stream comprising unreacted $Cl_2$, monochlorinated propenes and HCl, the HCl is separated from the stream as anhydrous HCl and the unreacted Cl2 is separated from the stream and recycled to the chlorination step.

10. The process of claim 1, wherein the at least one chlorination step generates a bottom stream comprising trichloropropane isomers, tetrachloropropane isomers, pentachloropropane isomers and unreacted PDC.

11. The process of claim 10, wherein the trichloropropane isomers, tetrachloropropane isomers and unreacted PDC are separated from the bottoms stream and recycled back to the chlorination step.

12. The process of claim 10, wherein the pentachloropropane isomers are separated from the bottoms stream and further separated into a first stream comprising 1,1,2,2,3-pentachloropropane and 1,1,1,2,2-pentachloropropane and a second stream comprising 1,1,2,3,3-pentachloropropane.

13. The process of claim 12, comprising caustic cracking 1,1,2,2,3-pentachloropropane and 1,1,1,2,2-pentachloropropane to provide 1,1,2,3-tetrachloropropene and 2,3,3,3-tetrachloropropene.

14. The process of claim 1, wherein the dehydrochlorination step is conducted first.

15. The process of claim 1, wherein the one or more chlorinated alkanes are generated for use in the process.

* * * * *